(12) United States Patent
Ayotte et al.

(10) Patent No.: US 10,309,884 B2
(45) Date of Patent: Jun. 4, 2019

(54) PREDICTING SEMICONDUCTOR PACKAGE WARPAGE

(71) Applicant: International Business Machines Corporation, Armonk, NY (US)

(72) Inventors: Stephen P. Ayotte, Bristol, VT (US); Eric G. Liniger, Sandy Hook, CT (US); Travis S. Longenbach, Essex Junction, VT (US)

(73) Assignee: International Business Machines Corporation, Armonk, NY (US)

( * ) Notice: Subject to any disclaimer, the term of this patent is extended or adjusted under 35 U.S.C. 154(b) by 11 days.

(21) Appl. No.: 15/627,514

(22) Filed: Jun. 20, 2017

(65) Prior Publication Data

US 2017/0284913 A1 Oct. 5, 2017

Related U.S. Application Data

(62) Division of application No. 14/672,331, filed on Mar. 30, 2015, now Pat. No. 9,772,268.

(51) Int. Cl.
*G01N 3/42* (2006.01)
*G01M 5/00* (2006.01)
(Continued)

(52) U.S. Cl.
CPC ............ *G01N 3/42* (2013.01); *G01M 5/0075* (2013.01); *G01N 3/20* (2013.01);
(Continued)

(58) Field of Classification Search
CPC .......... G01N 3/42; G01N 3/20; G01M 5/0075
See application file for complete search history.

(56) References Cited

U.S. PATENT DOCUMENTS

| 4,852,029 A | 7/1989 | Pope et al. |
| 5,184,517 A | 2/1993 | Kelzer |

(Continued)

FOREIGN PATENT DOCUMENTS

WO 9534805 12/1995

OTHER PUBLICATIONS

Birzer et al., "Reliability Investigations of Leadless QFN Packages until End-of-Life with Application-Specific Board-Level Stress Tests", 2006 IEEE, 2006 Electronic Components and Technology Conference, pp. 594-600.

(Continued)

*Primary Examiner* — David Z Huang
(74) *Attorney, Agent, or Firm* — Gibb & Riley, LLC; Steven J. Meyers

(57) ABSTRACT

A method for predicting the electrical functionality of a semiconductor package, the method includes performing a first stiffness test for a first semiconductor package, receiving failure data for the first semiconductor package, the failure data includes results of an electrical test performed after the first semiconductor package is assembled on a printed circuit board, generating a database comprising results of the first stiffness test as a function of the failure data for the first semiconductor package, performing a second stiffness test for a second semiconductor package, identifying a unique result from the results of the first stiffness test in the database, the unique result aligns with a result of the second stiffness test, and predicting a failure data for the second semiconductor package based on the failure data for the first semiconductor package which corresponds to the unique result of the first stiffness test identified in the database.

20 Claims, 7 Drawing Sheets

(51) Int. Cl.
  *G01N 3/20* (2006.01)
  *G01N 33/00* (2006.01)
  *G01R 31/28* (2006.01)

(52) U.S. Cl.
  CPC ........... *G01N 2033/0078* (2013.01); *G01N 2033/0081* (2013.01); *G01N 2033/0095* (2013.01); *G01N 2203/0222* (2013.01); *G01R 31/2896* (2013.01)

(56) References Cited

U.S. PATENT DOCUMENTS

| | | |
|---|---|---|
| 5,567,884 A | 10/1996 | Dickinson et al. |
| 5,601,364 A | 2/1997 | Ume |
| 5,949,682 A | 9/1999 | Dickinson et al. |
| 7,231,833 B2 | 6/2007 | McAllister et al. |
| 7,543,507 B2 | 6/2009 | Li et al. |
| 8,152,364 B2 | 4/2012 | Petitdidier et al. |
| 8,710,629 B2 * | 4/2014 | Bai ............ H01L 23/562 257/618 |
| 2009/0140053 A1 | 6/2009 | Yamazaki et al. |
| 2011/0248739 A1 | 10/2011 | Kim et al. |
| 2012/0135547 A1 | 5/2012 | Hsieh et al. |
| 2015/0123692 A1 | 5/2015 | Woo et al. |

OTHER PUBLICATIONS

Lou et al., "The Effect of Strain Rate and Strain Range on Bending Fatigue Test", 2008 International Conference on Electronic Packaging Technology & High Density Packaging (ICEPT-HDP 2008), IEEE, 5 page.
Meyyappan et al., "Effects of Glue on the Bend Performance of Flip Chip Packages", IEEE Transactions on Components and Packaging Technologies, vol. 31, No. 3, Sep. 2008, pp. 670-677.
Pang et al., "Isothermal Cyclic Bend Fatigue Test Method for Lead Free Solder Joints", 2006 IEEE, pp. 1011-1017.
Skipor, "Mechanical Bending Fatigue Reliability and Its Application to Area Array Packaging", 2001 IEEE, 2001 Electronic Components and Technology Conference, 7 pages.
Office Action Communication, U.S. Appl. No. 14/672,331, dated Apr. 21, 2017, pp. 1-7.
Notice of Allowance Communication, U.S. Appl. No. 14/672,331, dated May 23, 2017, pp. 1-15.

* cited by examiner

Section A-A

PREDICTING SEMICONDUCTOR PACKAGE WARPAGE

CROSS-REFERENCE TO RELATED APPLICATIONS

The present application claims the benefit under 35 U.S.C. § 120 as a division of U.S. patent application Ser. No. 14/672,331, filed on Mar. 30, 2015, now U.S. Pat. No. 9,772,268, issued on Sep. 26, 2017, the entire teachings of which are incorporated herein by reference.

BACKGROUND

The present invention generally relates to semiconductor packages, and more particularly, to predicting the at temperature warpage of the semiconductor packages.

A semiconductor package is an electronic package with an integrated circuit or die mounted on a substrate with a lid. The semiconductor package has external electronic connections. A semiconductor package may warp within a predetermined temperature range due to the difference or mismatch in the coefficient of thermal expansion (CTE) of the integrated circuit and the substrate. A semiconductor package may also be referred to as a semiconductor chip package, a module, a multi-chip module, a multi-chip package, a chip, an electronic chip, a flip chip, a flip chip package, a stacked chip, an integrated circuit package, a semiconductor device assembly, an encapsulation, and other names.

SUMMARY

According to one embodiment of the present invention, a method of predicting a warpage of a semiconductor package is provided. The method of predicting the warpage of the semiconductor package may include performing a stiffness test including stabilizing a portion of the semiconductor package in a fixture, such that a cantilevered portion remains, applying a force to a corner of the cantilevered portion causing the semiconductor package to bend, measuring the applied force, measuring a deflection of the corner of the cantilevered portion, recording stiffness test results comprising the applied force as a function of the deflection of the corner, and using the stiffness test results to predict the warpage of the semiconductor package.

According to another embodiment of the present invention, a method for predicting the electrical functionality of a semiconductor package is provided, the method may include performing a first stiffness test for a first semiconductor package, receiving failure data for the first semiconductor package, the failure data includes results of an electrical test performed after the first semiconductor package is assembled on a printed circuit board, generating a database comprising results of the first stiffness test for the first semiconductor package as a function of the failure data for the first semiconductor package, performing a second stiffness test for a second semiconductor package, the second stiffness test is carried out in a substantially similar manner as the first stiffness test, identifying a unique result from the results of the first stiffness test in the database, the unique result aligns with a result of the second stiffness test, and predicting a failure data for the second semiconductor package based on the failure data for the first semiconductor package which corresponds to the unique result of the first stiffness test identified in the database.

According to another embodiment of the present invention, a computer system for predicting the electrical functionality of a semiconductor package is provided, the computer system includes one or more computer processors, one or more computer-readable storage media, and program instructions stored on one or more of the computer-readable storage media for execution by at least one of the one or more processors, the program instructions include program instructions to perform a first stiffness test for a first semiconductor package, program instructions to receive failure data for the first semiconductor package, the failure data comprises results of an electrical test performed after the first semiconductor package is assembled on a printed circuit board, program instructions to generate a database comprising results of the first stiffness test for the first semiconductor package as a function of the failure data for the first semiconductor package, program instructions to perform a second stiffness test for a second semiconductor package, the program instructions to perform the second stiffness test are substantially similar to the program instructions to perform the first stiffness test, program instructions to identify a unique result from the results of the first stiffness test in the database, the unique result aligns with a result of the second stiffness test, and program instructions to predict a failure data for the second semiconductor package based on the failure data for the first semiconductor package, which corresponds to the result of the first stiffness test identified in the database.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings, in which.

Figure 1:
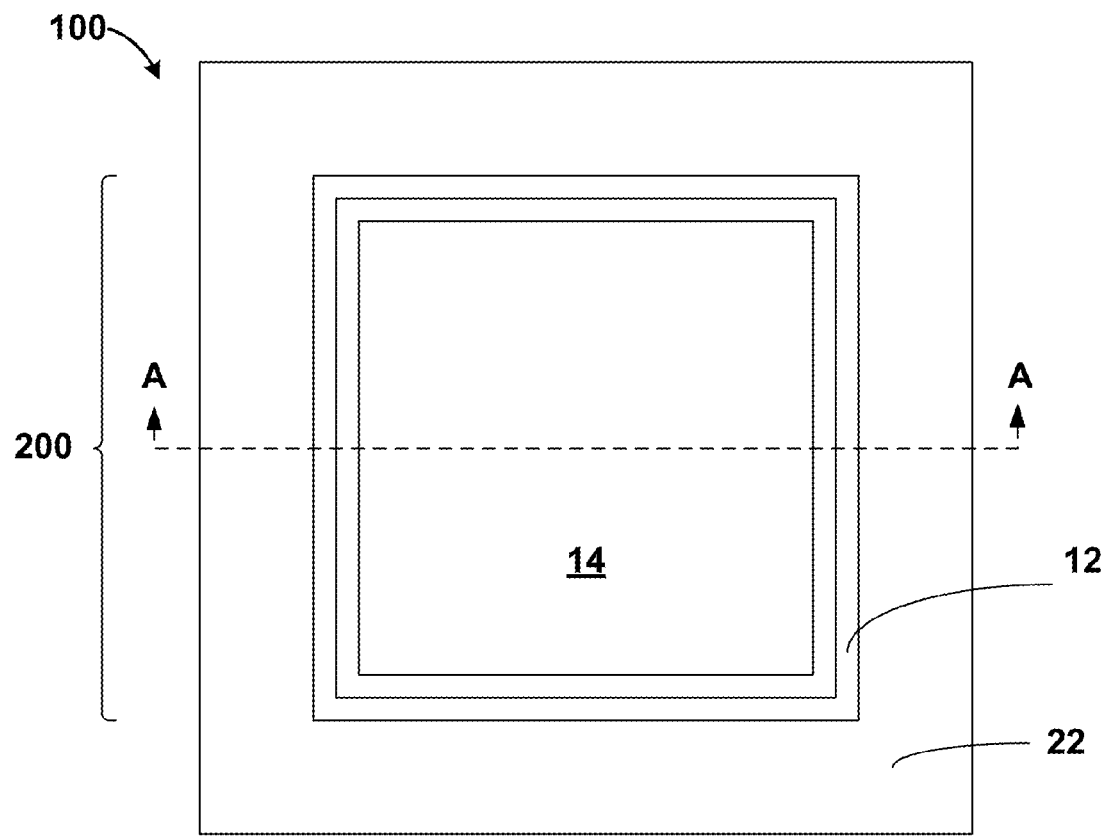
FIG. 1 is a top view of a semiconductor package on a printed circuit board.

Elements of the figures are not necessarily drawn to scale and are not intended to portray specific parameters of the invention. For clarity and ease of illustration, the scale of elements may be exaggerated. The detailed description should be consulted for accurate dimensions. The drawings are intended to depict only typical embodiments of the invention, and therefore should not be considered as limiting the scope of the invention. In the drawings, like numbering represents like elements.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms, and should not be construed as limited to the exemplary embodiments set forth herein. In the description, details of well-known features and techniques may be omitted to avoid unnecessarily obscuring the presented embodiments.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper", "lower", "right", "left", "vertical", "horizontal", "top", "bottom", and derivatives thereof shall relate to the disclosed structures and methods, as oriented in the drawing figures. The terms "overlying", "atop", "on top", "positioned on", or "positioned atop" mean that a first element, such as a first structure, is present on a second element, such as a second structure, wherein intervening elements, such as an interface structure may be present between the first element and the second element. The term "direct contact" means that a first element, such as a first structure, and a second element, such as a second structure, are connected without any intermediary conducting, insulating, or semiconductor layers at the interface of the two elements.

In the interest of not obscuring the presentation of embodiments of the present invention, in the following detailed description, some processing steps or operations that are known in the art may have been combined together for presentation and for illustration purposes and in some instances may not have been described in detail. In other instances, some processing steps or operations that are known in the art may not be described at all. It should be understood that the following description is rather focused on the distinctive features or elements of various embodiments of the present invention.

The present invention generally relates to semiconductor packages, and more particularly to predicting the at temperature warpage or nonflatness of a semiconductor package. The ability to predict the at temperature warpage of the semiconductor package may improve performance, reliability, and yield. One way to predict the at temperature warpage of the semiconductor package may include measuring a stiffness of the semiconductor package from which a correlation may be drawn between stiffness and the at temperature warpage. The correlation between stiffness and at temperature warpage may be used to predict reliability, performance, and yield of the semiconductor package after it is assembled on a printed circuit board. One embodiment by which to predict the at temperature warpage of the semiconductor package is described in detail below by referring to the accompanying FIGS. 1-9.

Figure 2:
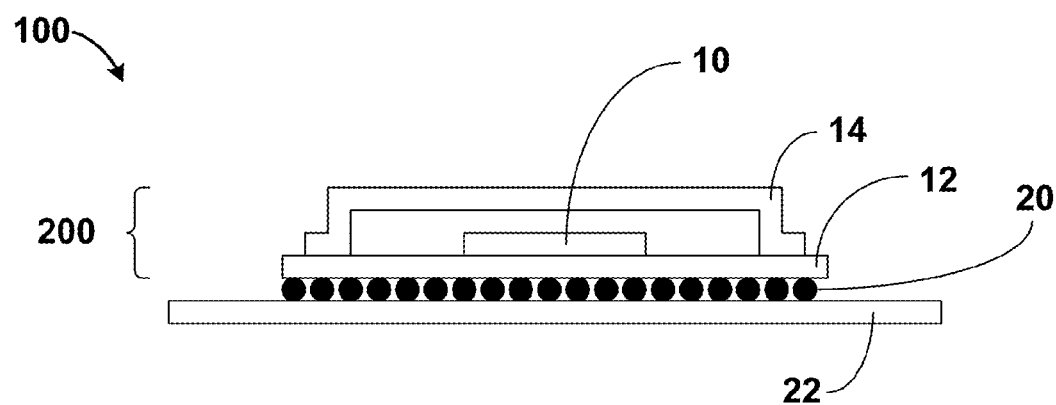
FIG. 2 is a vertical cross-sectional view of the semiconductor package and the printed circuit board along section line A-A.

Referring now to FIGS. 1 and 2, a semiconductor assembly 100 (hereinafter "assembly") is shown. The assembly 100 may include a semiconductor package 200 (hereinafter "package") assembled on a printed circuit board 22 (hereinafter "PCB"). The package 200 may be electrically and physically connected to the PCB 22 using a plurality of solder connections 20. A typical joining sequence to create the solder connections 20 may begin with depositing or applying a plurality of solder balls on a plurality of bonding pads on the package 200. The solder balls are then heated to a temperature sufficient to cause them to reflow. Next, the package 200, including the plurality of solder balls, is aligned to and placed on a package site on the PCB 22. In doing so, the solder balls contact a corresponding plurality of bonding pads on the PCB 22. The solder balls are again heated to a temperature sufficient to cause them to reflow, creating the solder connections 20. The final solder connections 20 may electrically connect and physically join the package 200 to the PCB 22. An example of the solder connections 20 includes controlled collapse chip connection (also known as C4 or flip-chip connection).

Any known technique may be used to heat the assembly 100 and cause the solder balls to reflow. In an embodiment, a typical reflow oven can use a controlled time-temperature profile to heat the assembly 100 and cause the solder balls to reflow. The reflow oven can include heating elements, for example infrared heating elements, to provide the required heat. Generally, a temperature above the reflow temperature of the solder balls is used to ensure complete reflow. In an embodiment, a temperature ranging from about 218° C. to about 260° C. can be applied to cause the solder balls to reflow. The reflow temperature or temperature at which the package 200 is joined to the PCB 22 may subsequently be referred to as the "at temperature."

The solder balls referred to above may include one or more solder alloys, for example, lead-based solder alloys or lead-free solder alloys. Non-limiting examples of lead-free solder alloys may include tin-silver (Sn/Ag) and tin-silver-copper (Sn/Ag/Cu). The specific solder alloy used to form the solder connections 20 may dictate the required reflow temperature. The semiconductor packages that use the solder balls as mentioned above may also be referred to as a ball grid array, flip chip, and other known names.

The package 200 may include an integrated circuit 10, a substrate 12, and a lid 14. The integrated circuit 10 may include a semiconductor chip or silicon die, which may be electrically connected and physically joined to a top surface of the substrate 12 in a similar fashion to the joining technique described above, for example, by a C4 or flip-chip connection.

The substrate 12, also known as a carrier, may be a ceramic substrate, a composite substrate, or a laminate substrate. In an embodiment, the substrate 12 is an organic laminate substrate. Laminate substrates may be very similar to printed circuit boards in that similar materials and build processes are used. Laminate substrates may be preferable for their relatively lower cost and increased electrical performance due to the use of copper conductors and lower-dielectric-constant insulator materials. Laminate substrates may be very similar to traditional printed circuit boards, however laminate substrates may have significantly higher per-layer wiring densities. For example, the substrate 12 may include a structure including four epoxy-glass-reinforced copper layers jacketed by four unreinforced build-up dielectric copper layers on each side. Typically, the copper layers of the substrate may include thick full metal layers, referred to as power planes, and thinner subplanes, referred to as power islands. The integrated circuit 10 is generally smaller than the substrate 12 to which it is attached. For example, in an embodiment, the integrated circuit 10 may be about approximately 15 mm×15 mm square, and the substrate 12 may be approximately 45 mm×45 mm square.

The lid 14 may generally be made from a metal and may be secured to the substrate 12 such that it covers and protects the integrated circuit 10. More specifically, the lid 14 may be physically attached or secured to a perimeter or periphery of the substrate 12 using a sealant applied directly to the top surface of the substrate 12 or, alternatively, to a bottom surface of the lid 14. Typically, the size and shape of the lid 14 may be specifically designed not to contact the integrated circuit 10 while leaving a space between a top surface of the integrated circuit 10 and an inner surface of the lid 14. In addition to providing physical protection, the lid 14 may also serve a heat transfer function by conducting heat from the integrated circuit 10 during operation. In order to conduct heat away from the integrated circuit 10, a thermal interface material may be applied directly to the top surface of the integrated circuit 10 to fill the small space between the integrated circuit 10 and the lid 14. The thermal interface material is used to create a thermal connection between the integrated circuit 10 and the lid 14 for purposes of heat transfer. In many instances, a heat sink (not shown) is commonly attached to an exterior surface of the lid 14 to further improve the dissipation of heat away from the integrated circuit 10. It should be noted that, while the embodiment depicted in the figures includes one integrated circuit 10, any number of integrated circuits may be included in the package 200.

The various components of the package 200 described above may each have a different coefficient of thermal expansion (CTE). For example, the substrate 12 may have a CTE approximately seven times that of the integrated circuit 10, and the integrated circuit 10 and the substrate 12 may together have a combined CTE of approximately four to five times that of the lid 14. For example, in an embodiment, the integrated circuit 10 may have a CTE of about 2 to 3 ppm/° C. while the substrate 12 may have an average CTE of about 25 ppm/° C. Additional examples of CTEs for relevant materials are included below in table 1. The difference between CTEs of the various components of the package 200 may alternatively be described as a CTE mismatch.

TABLE 1

Exemplary Coefficients of Thermal Expansion

| Material | CTE (ppm/° C.) |
|---|---|
| Silicon | 3.2 |
| Alumina | 6 to 7 |
| Copper | 16.7 |
| Tin-lead Solder | 27 |
| E-glass | 54 |
| S-glass | 16 |
| Epoxy resins | 15-100 |
| Silicon Resins | 30-300 |

During assembly of the package 200 to the PCB 22, both the package 200 and the PCB 22 may be heated, melting the solder balls to form the soldered connections 20 and create the assembly 100, as described above. During heating, the substrate 12 may expand up to seven times greater than the expansion of the integrated circuit 10 as a result of the CTE mismatch between the two components. The CTE mismatch between the substrate 12 and the integrated circuit 10 may cause undesirable and unpredictable warping of the package 200. The variations in warpage experienced by the package 200 may be described in terms of the following shapes: saddle, frown, smile, potato chip, cowboy hat, along with other names. Warping of the package 200 is undesirable because it may result in broken electrical connections, which may be discovered during electrical testing carried out after the package 200 is assembled onto the PCB 22. More specifically, warpage of the package 200 may cause a portion of the package 200 to lift away from the PCB 22 resulting in "opens" by preventing one or more solder connections 20 from forming. Alternatively, warpage of the package 200 may cause a portion of the package 200 to bend towards the PCB 22 resulting in "shorts" by causing two or more solder balls of adjacent solder connections 20 to touch. In yet another alternative, the assembly 100 may be too stiff resulting in cracking of the substrate 12 caused by flexing during post-assembly handing of the assembly 100.

Therefore, a desired stiffness of the package 200 is dependent on a number of factors pertaining to the assembly of the package 200 onto the PCB 22. It has been envisioned by the inventors that the embodiments of the present invention described herein may be used to design and supply a package 200 design having a desired stiffness based on the assembly conditions when the package 200 is assembled onto the PCB 22.

Figure 3:
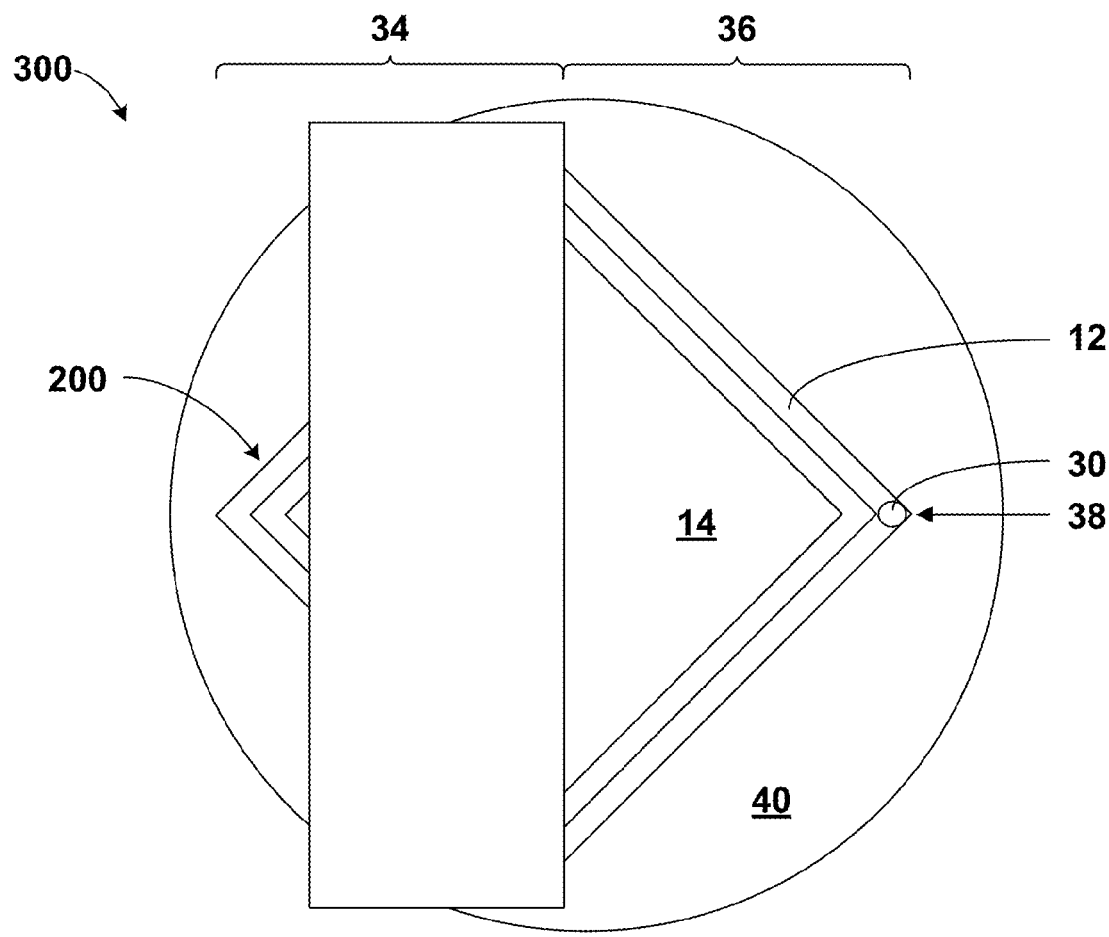
FIG. 3 is a top view of the semiconductor package and a flat plate according to an exemplary embodiment.
Figure 4:
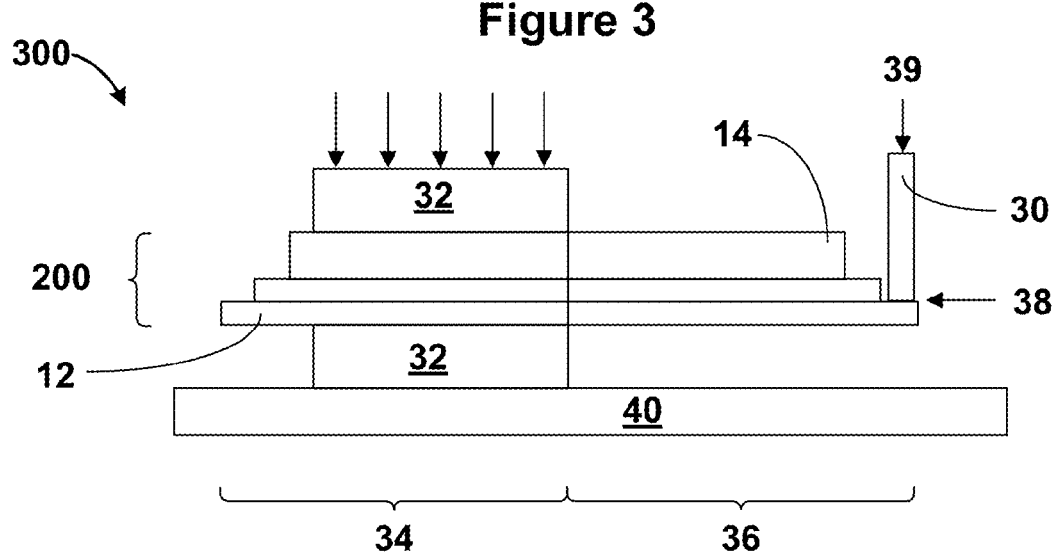
FIG. 4 is a side view of the semiconductor package and the flat plate according to an exemplary embodiment.

Referring now to FIGS. 3 and 4, a stiffness test structure 300 is shown. In an embodiment, the stiffness test structure 300 may include a work surface 40, two flat plates 32, and a test probe 30. The stiffness test structure 300 may be used to measure the stiffness of the package 200. The flat plates 32 may be used to stabilize a portion 34 of the package 200. Specifically, the flat plates 32 may be placed one beneath and one on top of the package 200 such that a cantilevered portion 36 of the package 200 remains generally unsupported. A clamping force may be applied to the flat plates 32 and the work surface 40 to firmly secure the package 200 to the work surface 40. The clamping force may be applied using any known device or technique, for example a C-clamp, capable of sufficiently securing the package 200 to the work surface 40 to prevent movement of the package 200 during stiffness testing.

In an embodiment, the portion 34 of the package 200 secured by the flat plates 32 may be approximately half of the package 200. Continuing in this embodiment, the cantilevered portion 36 is the other half of the package 200. Where and how the package 200 is secured to the work surface 40 is less critical than using a consistent method to generate a repeatable test and comparable results. In an embodiment, for example, the cantilevered portion 36 of the package 200 may preferably be exactly half of the package 200 defined by two adjacent sides and a diagonal line extending between two opposite corners. As illustrated, the package 200 may be clamped along a centerline drawn between two opposite corners. The clamping from corner to corner may ensure maximum protrusion of the surface to be tested, i.e. the protruding corner, therefore ensuring that the value obtained is representative of the free motion forces that a corner experiences when exposed to temperature during assembly. It should be noted that, while the embodiment depicted in the figures includes rectangular flat plates 32, the flat plates 32 may be any shape suitable to secure the portion 34 of the package 200, such that the cantilevered portion 36 of the package 200 remains generally unsupported. In an embodiment, the solder connections 20 may be removed from the package 200 prior to securing the package 200 to the flat plates 32.

The test probe 30 may be a device capable of traveling in a substantially linear motion, which is perpendicular to the package 200. In an embodiment, the test probe 30 may be positioned on a corner 38 of the cantilevered portion 36. More specifically, the test probe 30 may be in direct contact with the substrate 12 at the corner 38. Preferably, the test probe 30 does not contact the lid 14.

During stiffness testing the test probe 30 may apply a force 39 causing the package 200 to bend or flex, resulting in the deflection of the corner 38. Meanwhile, the stiffness test structure 300, or more specifically a computer from which the stiffness test structure 300 is operated, may measure the force 39 as a function of deflection of the corner 38 of the package 200. Exemplary test results are described below with reference to FIG. 6. It should be noted that the package 200 is sufficiently secured to the work surface 40 to prevent movement of the cantilevered portion 36 of the package 200 during stiffness testing.

Figure 5:
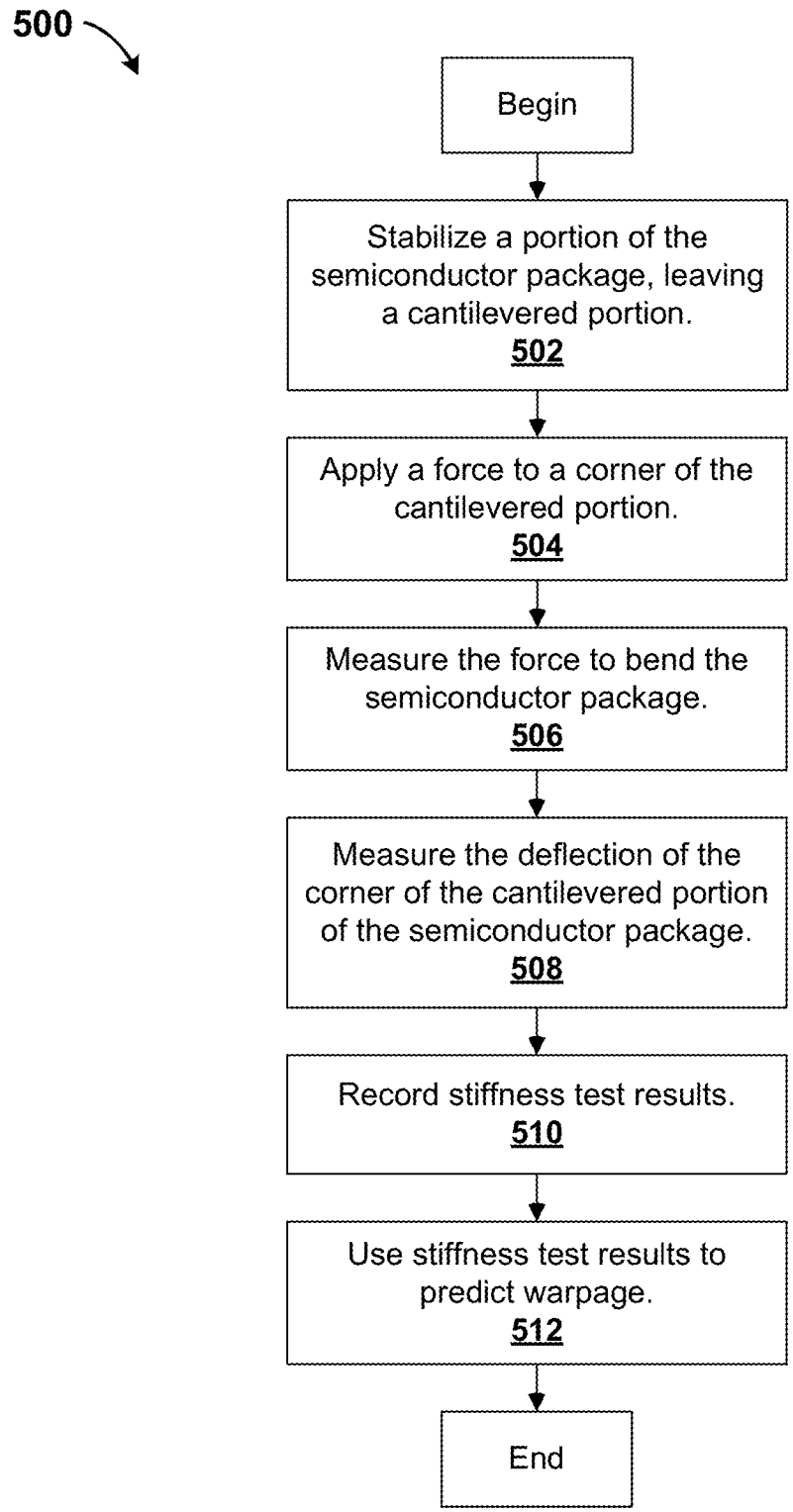
FIG. 5 is a test sequence according to an exemplary embodiment.

Referring now to FIG. 5, and with continued reference to FIGS. 1-4, a test sequence 500 is shown according to an embodiment. In general, the test sequence 500 may be carried out using the stiffness test structure 300, or similar static testing equipment, as described above with reference to FIGS. 3 and 4. The test sequence 500 may begin with stabilizing the portion 34 of the package 200 such that the cantilevered portion 36 of the package 200 remains generally unsupported (step 502). In a preferred embodiment, the portion 34 of the package 200, which is stabilized, includes half of the package 200 along a diagonal centerline extending between two corners of the package 200. The test sequence 500 may continue with the application of the force 39 to the corner 38 of the cantilevered portion 36, at (step 504). More specifically, the test probe 30, moving a predefined fixed distance in a linear motion at a constant rate, will push downward on the corner 38 and cause it to deflect.

Figure 6:
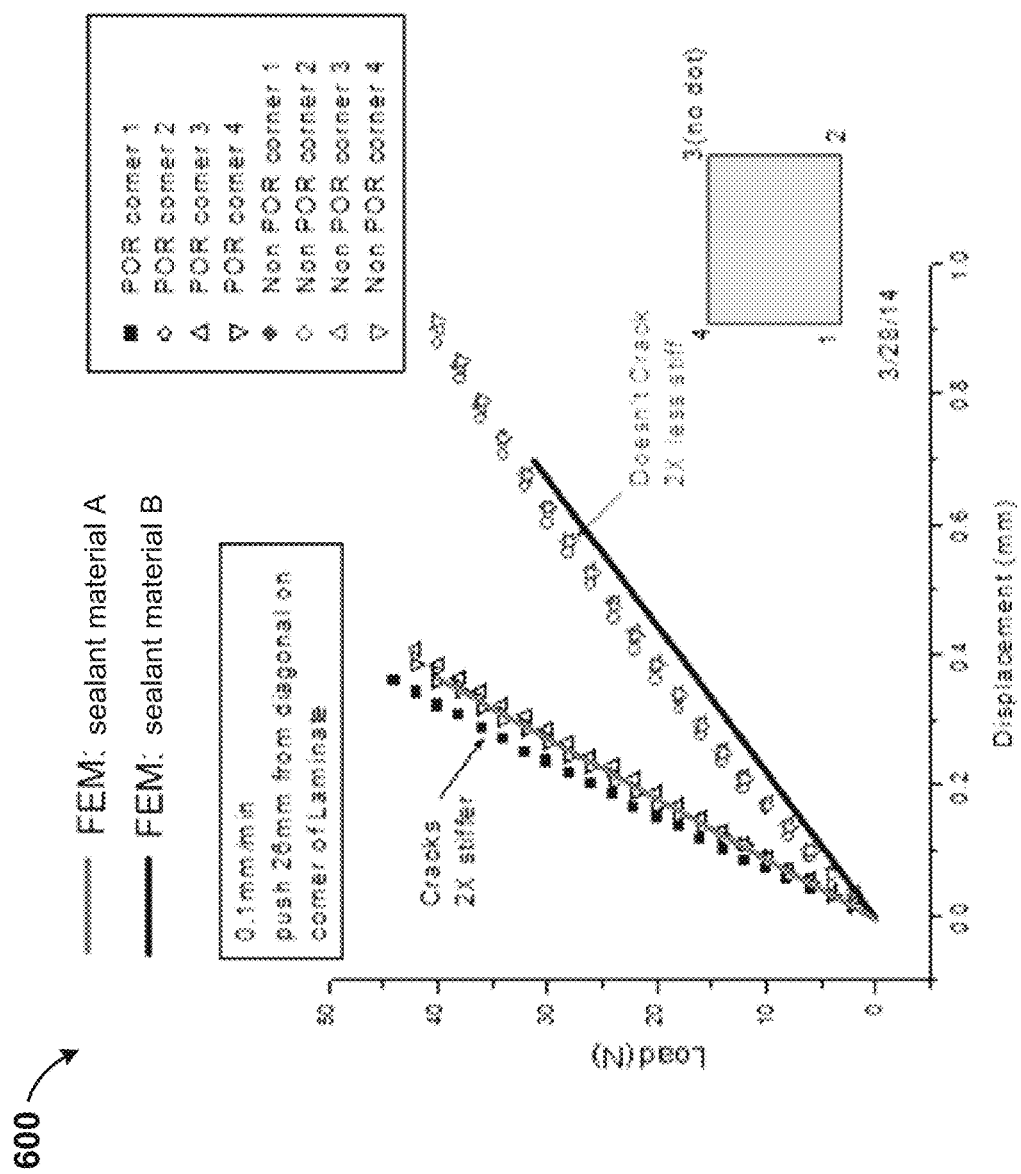
FIG. 6 is a graph of displacement versus load, according to an exemplary embodiment.

The test sequence 500 may continue with the application of the force 39 to the corner 38. As the test probe 30 applies the force 39 to the corner 38, the static testing equipment measures the force 39 (e.g. Newtons) required to bend the package 200, otherwise known as a reaction force (step 506). The deflection (e.g. mm) of the corner 38 may be simultaneously measured as the force 39 is applied (step 508). Stiffness test results may be compiled and recorded, either during the stiffness testing or after completion of the test (step 510). In an embodiment, the stiffness test results may include the force 39 as a function of the deflection of the corner, as illustrated in FIG. 6. The stiffness test results may subsequently be used (step 512), to predict warpage of the package 200. For example, a stiffer package 200 may require a higher force 39 to deflect the corner 38. Similarly, the force 39 measured during stiffness testing may indicate a relative stiffness of a particular package. As such, stiffness characteristics may be recorded with respect to the properties of each package.

In an embodiment, the stiffness test results may include properties or components of the package 200, such as laminate shape, size, and composition; die shape, size, and composition; lid shape, size, and composition; and sealant amount, pattern, and composition. For example, packages may differ in size and placement of the electrical connection circuitry on the substrate 12, in the material and shape of the lid 14, and in the method of attachment of the lid 14. In an exemplary embodiment, the stiffness test results can be used to predict another warpage of another semiconductor package, based on a comparison between the properties of the package 200 and the properties of the other semiconductor package. The stiffness test results for different package designs having different properties can be compared to determine what effect, if any, a particular property has on stiffness. Using the test results, the stiffness of a particular package design may be adjusted to achieve a stiffer or more flexible package design by modifying one or more of the package properties.

In an exemplary embodiment, the test sequence 500 may be performed using a stiffness test structure 300 that is housed in a temperature controlled environment, such as, for example, a temperature controlled chamber or oven. Doing so allows for the stiffness test results to be obtained with respect to any temperature, more specifically, increased temperatures simulating the reflow process described above.

Finally, the test sequence 500 may be conducted one or more times on each of the four corners 38 of the package 200. In an embodiment, the test sequence 500 may be conducted at least three times on each of the four corners 38 of the package 200. The test sequence 500 is repeated to improve accuracy and consistency in the recorded test results.

In an embodiment, after conducting stiffness testing, the package 200 may be assembled to PCB 22, in a similar fashion as described above with reference to FIGS. 1 and 2. After the package 200 is assembled to the PCB 22, the assembly 100, specifically the package 200, may undergo electrical testing. In an embodiment, the electrical testing may include electrical connectivity testing and electrical functionality testing. Results from the electrical testing may be in the form of electrical failure data, which may include, but are not limited to, type of electrical failure (e.g. "opens" or "shorts") and the location on the package 200 where the electrical failure is located. The electrical failure data of the assembly 100, specifically of the package 200, may be recorded along with the stiffness test results.

The stiffness test results and the electrical failure data may be used to quantify how different package designs respond to stresses and strains applied during assembly. Similarly, stiffness test results and electrical failure data for a plurality of packages, for example, the package 200, may be used to predict the at temperature warpage of a new package design, as described in greater detail below with reference to FIG. 8. With respect to the present embodiment, it should be noted that a strong correlation exists between the electrical failure data and the at temperature warpage as described above with reference to FIGS. 1 and 2.

Referring now to FIG. 6, and with continued reference to FIGS. 3-5, a graph 600 illustrating the stiffness test results is shown, according to an embodiment. The x-axis of the graph 600 shows a deflection in mm of the corner 38 of the package 200. The test probe 30 may move the corner 38 these distances during the stiffness testing. The y-axis of the graph 600 shows the force 39 ("load"), in Newtons (hereinafter "N"), applied to the corner 38 during stiffness testing.

The graph 600 illustrates stiffness test results for two different package designs, like the package 200. Each of the two package designs is substantially similar except the lid 14 for each package 200 design is attached to the substrate 12 using different sealant materials. In the present example, one package is assembled with sealant material A and the other package is assembled with sealant material B. Based on the graph 600, the package design using sealant material A is recognized as being the stiffer of the two packages, as evidenced by the angle or slope of the data points. Stated differently, the package design with sealant material A requires more force 39 to deflect the corner 38 and is therefore stiffer than the package design with sealant material B. Therefore, based on the test results and the graph 600, the package design with sealant material A is predicted to have less at temperature warpage and may have improved performance, reliability, and yield compared to the package design with sealant material B.

The stiffness test structure 300 and the test sequence 500 may have advantages over traditional methods for testing a particular package for warpage. Traditional methods may include techniques like Shadow Moire and finite element analysis. Shadow Moire is a proprietary technique that can be time intensive and costly. Use of the stiffness test structure 300 and the test sequence 500 costs less and is generally quicker than traditional Shadow Moire techniques. Finite element analysis (hereinafter "FEA") modeling can be used to predict some warping and failure modes, and requires specialized skills, high computing power, and large amounts of information surrounding failures in order to be useful. The stiffness test structure 300 with the test sequence 500 requires significantly less computing power or engineering time compared to finite element analysis to predict at temperature warpage of the package 200. Finally, the present invention uses an approach that may be easier to implement and to produce relevant stiffness test data.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus, or other device to produce a computer implemented process, such that the instructions that execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 7:
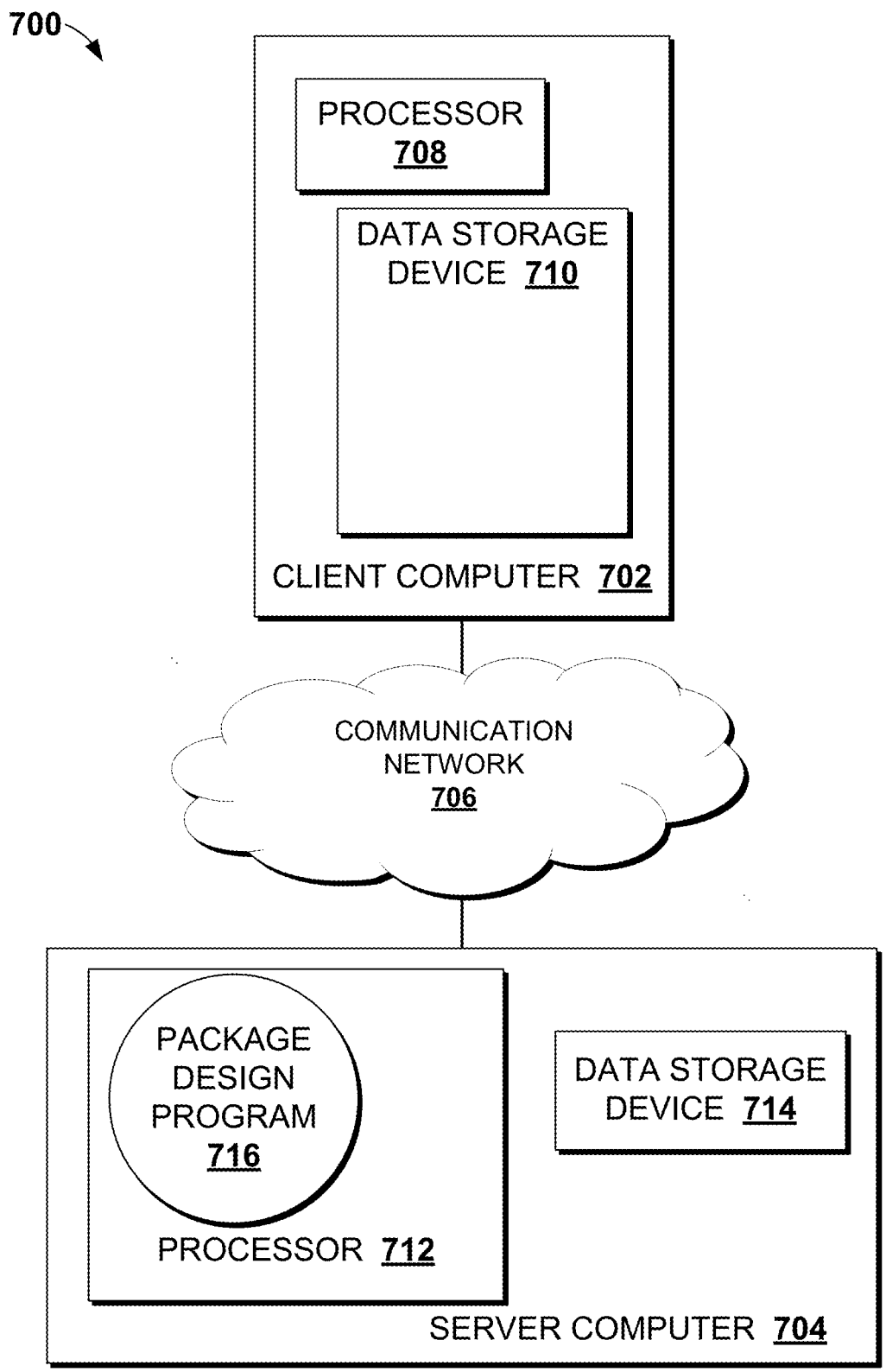
FIG. 7 is a functional block diagram illustrating a system for predicting warpage of a semiconductor package in a networked computer environment, in accordance with an exemplary embodiment.

Referring now to FIG. 7, a functional block diagram illustrating a system 700 for predicting the electrical functionality of a semiconductor package in a networked computer environment, in accordance with an embodiment of the present invention is shown. The system 700 may include a client computer 702 and a server computer 704. The client computer 702 may communicate with the server computer 704 via a communications network 706 (hereinafter "network"). The client computer 702 may include a processor 708 and a data storage device 710 that is enabled to interface with a user and communicate with the server computer 704. The server computer may also include a processor 712 and a data storage device 714. The processor 712 is enabled to run a package design program 716. In an embodiment, the client computer 702 may operate as an input device including a user interface while the package design program 716 may run primarily on the server computer 704. It should be noted, however, that processing for the package design program 716 may, in some instances be shared amongst the client computer 702 and the server computer 704 in any ratio. In another embodiment, the package design program 716 may operate on more than one server computer 704, client computer 702 or some combination of server computers 704 and client computers 702 for example, a plurality of client computers 702 communicating across the network 706 with a single server computer 704.

The network 706 may include wired connections, wireless connections, fiber optic connections, or some combination thereof. In general, the network 706 can be any combination of connections and protocols that will support communications between the client computer 702 and the server computer 704. The network 706 may include various types of networks, such as, for example, a local area network (LAN), a wide area network (WAN) such as the Internet, a telecommunication network, a wireless network, a public switched network, and/or a satellite network.

In various embodiments, the client computer 702 and/or the server computer 704 may be, for example, a laptop computer, tablet computer, netbook computer, personal computer (PC), a desktop computer, a personal digital assistant (PDA), a smart phone, a mobile device, or any programmable electronic device capable of communicating with the server computer 704 via the network 706. As described below with reference to FIG. 9, the client computer 702 and the server computer 704 may each include internal and external components.

In an embodiment, the system 700 may include any number of client computers 702 and/or server computers 704; however, only one of each is shown for illustrative purposes only. It may be appreciated that FIG. 7 provides only an illustration of one implementation and does not imply any limitations with regard to the environments in which different embodiments may be implemented. Many modifications to the depicted environment may be made based on design and implementation requirements.

In an embodiment, the package design program 716 may run on the server computer 704. The package design program 716 may be used to perform stiffness tests of a particular package design as well as electrical tests of the package and suggest alterations or modifications to the package design based on the prediction of electrical failure data for the package design. For example, a user may access the package design program 716 running on the server computer 704 via the client computer 702 and the network 706. The user may use the client computer 702 to input or provide the package design program 716 with the properties of semiconductor packages, and the package design program 716 will generate and provide the user, via the client computer 702 with a new semiconductor package design having a predefined stiffness based on the results of stiffness tests, the electrical test data, and properties of the semiconductor packages. The package design program 716 and associated method is described and explained in further detail below with reference to FIGS. 8 and 9.

Figure 8:
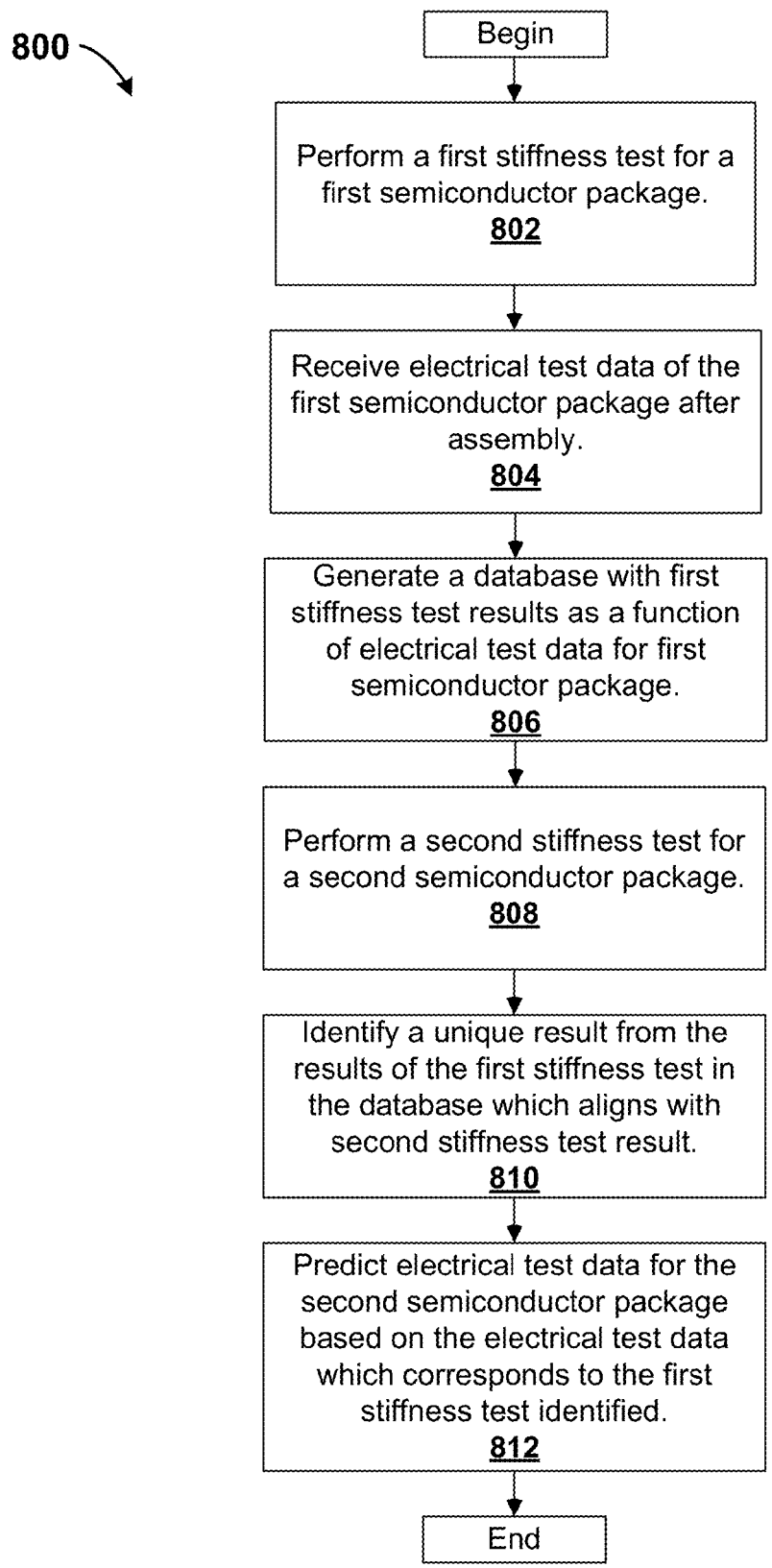
FIG. 8 is a flowchart depicting operational steps of a package design program within the networked computer environment of FIG. 7, in accordance with an exemplary embodiment.

Referring now to FIG. 8, and with continued reference to FIGS. 1-4, a flowchart 800 depicting operational steps of the package design program 716 for predicting the electrical functionality of a semiconductor package is shown in accordance with an embodiment of the present invention. The package design program 716 may begin by performing a first stiffness test for a first semiconductor package design (hereinafter "first package design") (step 802). In an embodiment, the first stiffness test may be carried out in a substantially similar manner as the test sequence 500 described above with reference to FIG. 5. Similar to above, stiffness test results may be compiled and recorded, either during stiffness testing or after completion of the first stiffness test. In embodiments in which a single semiconductor package design undergoes multiple rounds of stiffness testing in a repetitive sequence on all four corners, the stiffness test results may be compiled and recorded with respect to each corresponding corner of the package. After conducting stiffness testing, the first package design may be assembled to a printed circuit board, in a similar fashion as described above with reference to FIGS. 1 and 2.

After the first package design is assembled to a printed circuit board, the assembly, specifically the first package design, may undergo electrical testing. In an embodiment, the electrical testing may include electrical connectivity testing and electrical functionality testing. Results from the electrical testing may be in the form of electrical failure data, which may include, but are not limited to, type of electrical failure (e.g. "opens" or "shorts") and the location on the first package design where the electrical failure is located. The electrical failure data of the assembly, specifically the first package design, is then received by the package design program 716 (step 804).

The package design program 716 may then compile or collect the stiffness test results and the electrical failure data, both of the first package design. In an embodiment, the package design program 716 may prepare or generate a table or database including the stiffness test results as a function of the electrical failure data (step 806). More specifically, in an embodiment, the stiffness test results and the electrical failure data are each stored or located in a different table or database in which a pointer, or other known technique, is used to cross reference one with another.

In an embodiment, stiffness tests may be conducted on a variety of semiconductor package designs. The stiffness test results and the electrical failure data for each of the various semiconductor package designs may be included in the database.

The database may include the stiffness test results and the electrical failure data for the first package design in addition to stiffness test results and electrical failure data for various different package designs. For example, the database will include stiffness test results and the electrical failure data for each semiconductor package design tested.

The package design program 716 may perform or initiate a second stiffness test for a second semiconductor package design (hereinafter "second package design") (step 808). The second stiffness test may be carried out in a substantially similar manner as the test sequence 500 described above with reference to FIG. 5. Like above, stiffness test results may be compiled and recorded, either during testing or after completion of the first stiffness test. Unlike above, the second package design is not assembled to a printed circuit board.

Next, the package design program 716 may identify a unique result from the stiffness test results recorded in the database (step 810). The unique result identified in the database may align with the stiffness test results for the second package design. In an embodiment, the unique result may match one or more of the stiffness test results for the second package design. In another embodiment, the unique result may be similar to, without matching, one or more of the stiffness test results for the second package design. For example, in an embodiment, the unique result identified from the database may be within a predefined numerical tolerance of the stiffness test results for the second package design. In an embodiment, the unique result is a first stiffness test result entry in the database, which is closest in value to the second stiffness test result. In embodiments in which a single semiconductor package design undergoes multiple rounds of stiffness testing in a repetitive sequence on all fours corners, the unique result will preferably correspond to the same corner of the package.

After identifying the unique result, the package design program 716 may predict electrical failure data for the second package design (step 812). The electrical failure data for the second package design may be based on the unique result identified above. More specifically, because the database may preferably include a stiffness test result and electrical failure data for each package design tested, the package design program 716 may predict the electrical failure data for the second package design by "reading" the electrical failure data from the database which corresponds to the unique result. Therefore, the package design program 716 may predict the electrical test results, as such the electrical failure data, simply by accessing the database and comparing stiffness test results between the first package design and the stiffness test results of the second package design. Predicting the electrical test results of the second package design may be used to predict reliability, performance, and yield of the second package design after it is assembled on a printed circuit board.

In an alternative embodiment, the stiffness testing, in general, may be performed in a temperature controlled environment, as described above with reference to FIG. 5. In such cases, stiffness testing for both the first package design and the second package design may preferably be conducted in the same or substantially similar environments to ensure accuracy and consistency of the results. Furthermore, information about the stiffness testing environment, such as, for example, the temperature, may be compiled and recorded in the database alongside the stiffness test results and electrical failure data.

Similar to above, properties of the different package designs, such as laminate size, die size, lid shape, lid material, laminate composition, sealant material, and the amount of sealant used may also be recorded in the database with respect to the stiffness test results and electrical failure data.

In an alternative embodiment, the package design program 716 may suggest alterations or modifications to a particular package design based on the prediction of the electrical failure data for the second package design. For example, if the electrical failure data predicted for the second package design is unacceptable, or fails to meet a predefined threshold, the package design program 716 may suggest adjustments or changes to one or more of the package properties with the intention of improving the design. In addition, the package design program 716 may suggest alterations or modifications to a particular package design to change the stiffness of the particular package design. For example, if the stiffness test results for the second package design are unacceptable, or fail to meet a predefined threshold, the package design program 716 may suggest adjustments or changes to one or more of the package properties to either increase or decrease the stiffness of the particular package.

In yet another embodiment, the package design program 716 may suggest a new package design based on the stiffness test results, the electrical failure data, and the package properties compiled in the database. For example, the package design program 716 may suggest a new package design, in terms of its components and properties, which satisfies a predefined threshold, in terms of electrical test performance. Alternatively, according to another example, the package design program 716 may suggest a new package design, in terms of its components and properties, which satisfies a predefined threshold, in terms of stiffness. In other words, the stiffness test result for various different package designs can be compared with one another to determine what effect, if any, a particular package component or property has on the package design's stiffness.

Figure 9:
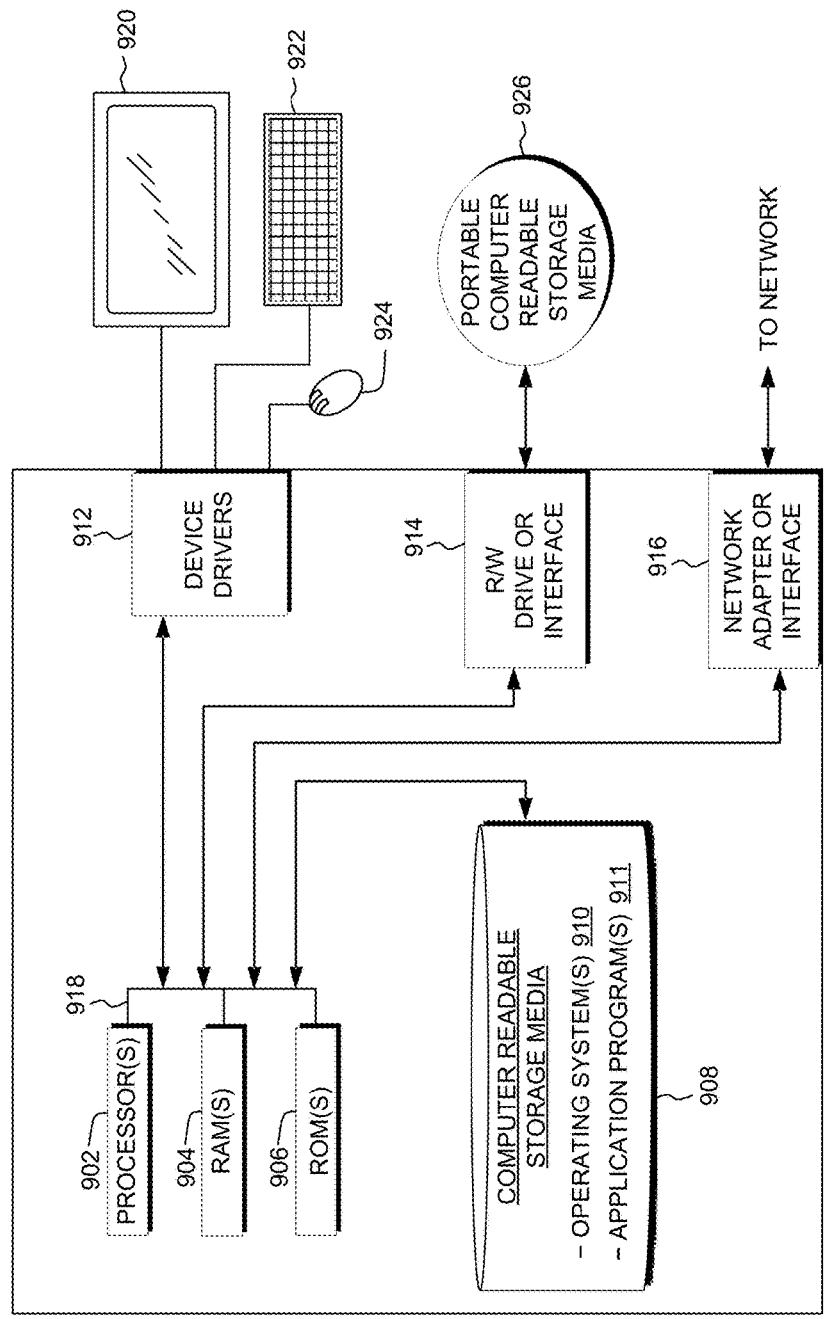
FIG. 9 is a functional block diagram of components of a server computer executing the package design program, in accordance with an exemplary embodiment.

Referring now to FIG. 9, a block diagram of components of a computing device, such as the client computer 702 or the server computer 704, of the system 700 of FIG. 7, in accordance with an embodiment of the present invention is shown. It should be appreciated that FIG. 9 provides only an illustration of one implementation and does not imply any limitations with regard to the environments in which different embodiments may be implemented. Many modifications to the depicted environment may be made.

The computing device may include one or more processors 902, one or more computer-readable RAMs 904, one or more computer-readable ROMs 906, one or more computer readable storage media 908, device drivers 912, a read/write drive or interface 914, and a network adapter or interface 916, all interconnected over a communications fabric 918. The communications fabric 918 may be implemented with any architecture designed for passing data and/or control information between processors (such as microprocessors, communications and network processors, etc.), system memory, peripheral devices, and any other hardware components within a system.

One or more operating systems 910, and one or more application programs 911, for example, the package design program 716, are stored on the one or more of the computer readable storage media 908 for execution by one or more of the processors 902 via one or more of the respective RAMs 904 (which typically include cache memory). In the illustrated embodiment, each of the computer readable storage media 908 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

The computing device may also include the R/W drive or interface 914 to read from and write to one or more portable computer readable storage media 926. Application programs 911 on the computing device may be stored on one or more of the portable computer readable storage media 926, read via the respective R/W drive or interface 914 and loaded into the respective computer readable storage media 908.

The computing device may also include the network adapter or interface 916, such as a TCP/IP adapter card or wireless communication adapter (such as, a 4G wireless communication adapter using OFDMA technology). Application programs 911 on the computing device may be downloaded to the computing device from an external computer or external storage device via a network (for example, the Internet, a local area network or other wide area network or wireless network) and network adapter or interface 916. From the network adapter or interface 916, the programs may be loaded onto computer readable storage media 908. The network may comprise copper wires, optical fibers, wireless transmission, routers, firewalls, switches, gateway computers, and/or edge servers.

The computing device may also include a display screen 920, a keyboard or keypad 922, and a computer mouse or touchpad 924. The device drivers 912 interface to the display screen 920 for imaging, to the keyboard or keypad 922, to the computer mouse or touchpad 924, and/or to the display screen 920 for pressure sensing of alphanumeric character entry and user selections. The device drivers 912, R/W drive or interface 914, and network adapter or interface 916 may include hardware and software (stored on computer readable storage media 908 and/or ROM 906).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Based on the foregoing, a computer system, method, and computer program product have been disclosed. However, numerous modifications and substitutions can be made without deviating from the scope of the present invention. Therefore, the present invention has been disclosed by way of example and not limitation.

What is claimed is:

1. A method of predicting warpage of a semiconductor package comprising:
performing a stiffness test comprising:
stabilizing a portion of the semiconductor package in a fixture, such that a cantilevered portion of the semiconductor package remains unstabilized,
applying a force to a corner of the cantilevered portion causing the semiconductor package to bend,
measuring the applied force, and
measuring a deflection of the corner of the cantilevered portion;
recording stiffness test results comprising the applied force as a function of the deflection of the corner; and
using the stiffness test results to predict the warpage of the semiconductor package.

2. The method of claim 1, wherein stabilizing the portion of the semiconductor package comprises:
stabilizing half of the semiconductor package defined by a diagonal line extending between two corners of the semiconductor package.

3. The method of claim 1, wherein the stiffness test is carried out in a temperature controlled chamber, and the temperature of the temperature controlled chamber is recorded along with the stiffness test results.

4. The method of claim 1, wherein a static testing machine is used to apply the force, measure the applied force, and measure the deflection of the corner.

5. The method of claim 1, wherein recording stiffness test results comprises:
recording properties of the semiconductor package comprising at least one of laminate size, die size, lid shape, lid material, laminate composition, sealant material, and amount of sealant used.

6. The method of claim 5, further comprising:
using the stiffness test results to predict warpage of another semiconductor package by comparing the properties of the semiconductor package and properties of the other semiconductor package.

7. The method of claim 1, further comprising:
repeating the stiffness test at least once for each corner of the semiconductor package.

8. A method, comprising:
performing a stiffness test of a semiconductor package, the stiffness test comprising:
stabilizing half of the semiconductor package in a fixture, such that an unstabilized half of the semiconductor package remains free to move,
applying a force to a corner of the unstabilized half of the semiconductor package causing the semiconductor package to bend,
measuring the amount of applied force, and
measuring the amount of deflection of the corner of the unstabilized half of the semiconductor package;
recording stiffness test results comprising the amount of applied force and the amount of deflection of the corner;
assembling the semiconductor package on a printed circuit board;
performing electrical testing of the semiconductor package after the semiconductor package is assembled on a printed circuit board, the electrical testing generating failure data; and
generating a database comprising results of the stiffness test for the semiconductor package and the failure data for the semiconductor package.

9. The method of claim 8, wherein half of the semiconductor package is defined by a diagonal line extending between two corners of the semiconductor package.

10. The method of claim 8, wherein the stiffness test is carried out in a temperature controlled chamber, and the temperature of the temperature controlled chamber is recorded along with the stiffness test results.

11. The method of claim 8, wherein a static testing machine is used to apply the force, measure the applied force, and measure the amount of deflection of the corner.

12. The method of claim 8, further comprising:
correlating the amount of applied force and the amount of deflection of the corner to predict warpage of the semiconductor package.

13. The method of claim 12, wherein the results of the stiffness test comprises:
properties of the semiconductor package comprising at least one of laminate size, die size, lid shape, lid material, laminate composition, sealant material, and amount of sealant used.

14. The method of claim 13, further comprising:
using the stiffness test results to predict warpage of another semiconductor package by comparing the properties of the semiconductor package and properties of the other semiconductor package.

15. The method of claim 8, further comprising:
repeating the stiffness test at least once for each corner of the semiconductor package.

16. A method, comprising:
performing a stiffness test of a semiconductor package, the stiffness test comprising:
stabilizing a portion of the semiconductor package in a fixture, such that a cantilevered portion of the semiconductor package remains free to move,
applying a force to a corner of the cantilevered portion of the semiconductor package causing the semiconductor package to bend,
measuring the amount of force applied to the corner of the cantilevered portion of the semiconductor package, and
measuring the amount of deflection of the corner of the cantilevered portion;
correlating the amount of force applied to the corner of the cantilevered portion and the amount of deflection of the corner of the cantilevered portion as results of the stiffness test for the semiconductor package; and
using the results of the stiffness test to predict warpage of the semiconductor package.

17. The method of claim 16, wherein stabilizing the portion of the semiconductor package comprises:
stabilizing half of the semiconductor package defined by a diagonal line extending between corners of the semiconductor package.

18. The method of claim 16, further comprising:
recording the results of the stiffness test in a database; and
recording properties of the semiconductor package comprising at least one of laminate size, die size, lid shape, lid material, laminate composition, sealant material, and amount of sealant used.

19. The method of claim 16, further comprising:
assembling the semiconductor package on a printed circuit board; and
performing electrical testing of the semiconductor package after the semiconductor package is assembled on a printed circuit board, the electrical testing generating failure data for the semiconductor package.

20. The method of claim 19, further comprising:
generating a database comprising results of the stiffness test for the semiconductor package and the failure data for the semiconductor package.

* * * * *